United States Patent [19]

Conetta et al.

[11] Patent Number: 4,753,979

[45] Date of Patent: Jun. 28, 1988

[54] SUBSTITUTED PIPERAZINONE LIGHT STABILIZERS

[75] Inventors: Thomas E. Conetta, Bethel, Conn.; Roger F. Malherbe, Yonkers; Roland A. E. Winter, Armonk, both of N.Y.

[73] Assignee: Ciba-Geigy Corporation, Ardsley, N.Y.

[21] Appl. No.: 929,589

[22] Filed: Nov. 12, 1986

Related U.S. Application Data

[62] Division of Ser. No. 588,462, Mar. 12, 1984, Pat. No. 4,650,870.

[51] Int. Cl.[4] ............................................ C07D 241/04
[52] U.S. Cl. .................................... 524/100; 524/102; 544/231; 544/357; 544/384
[58] Field of Search ..................... 544/357, 231, 384; 524/100, 102

[56] References Cited

U.S. PATENT DOCUMENTS 4,298,737 11/1981 Lai et al. ............................ 544/259

Primary Examiner—Glennon H. Hollrah
Assistant Examiner—James H. Turnipseed
Attorney, Agent, or Firm—Luther A. R. Hall

[57] ABSTRACT

Compounds of the formula $(T)_g$-E where T is a substituted 4-acyl-2-piperazinone group, g is 1 or 2 and E is a selected terminal or linking group, are effective light stabilizers for polyolefins and other organic polymers, particularly thermoset acrylic or alkyd acrylic resins.

6 Claims, No Drawings

SUBSTITUTED PIPERAZINONE LIGHT STABILIZERS

This is a divisional of application Ser. No. 588,462, filed on Mar. 12, 1984, U.S. Pat. No. 4,650,870, issued on Mar. 17, 1987.

BACKGROUND OF THE INVENTION

The present invention pertains to compounds containing a substituted 4-acyl-2-piperazinone moiety which are useful as light and heat stabilizers for organic materials and to stabilized compositions containing said compounds.

The hindered amine compounds having the 2,2,6,6-tetrasubstituted piperidinyl structure have long been known as effective light stabilizers for organic materials and have enjoyed considerable commercial success.

Such hindered amine light stabilizers are described in detail by H. J. Heller and H. R. Blattmann, Pure and Applied Chemistry, 36, 141–161 (1973).

Substituted 2-piperazinones useful as UV stabilizers for photodegradable plastics are described in U.S. Pat. Nos. 4,190,571; 4,292,240 and 4,298,737. The compounds clearly described therein all contain a secondary or tertiary amine group, which being strongly basic, makes said compounds unsuitable for many end-use applications. U.S. Pat. No. 4,190,571 mentions N-carboalkoxy (urethane) compounds in passing, but does not teach how such compounds might be prepared or what properties said urethane derivatives might possess.

Acylated hindered amine light stabilizers based on piperidine are described in U.S. Pat. Nos. 4,046,737 and 4,066,615.

DETAILED DISCLOSURE

This invention relates to compounds containing a substituted 4-acyl-2-piperazinone moiety which are useful as light stabilizers for organic polymers and to stabilized compositions containing said compounds.

The instant invention more particularly pertains to a light stabilizer compound of formula I $$(T-)_g E \qquad (I)$$

wherein
T is a group of the formula

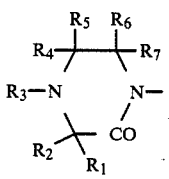

$R_1$ and $R_2$ are independently alkyl having 1 to 12 carbon atoms, cycloalkyl having 5 to 12 carbon atoms, alkenyl having 2 to 14 carbon atoms or aralkyl having 7 to 15 carbon atoms, $R_3$ is alkanoyl having 1 to 12 carbon atoms, alkenoyl having 3 to 8 carbon atoms or benzoyl, $R_4$ and $R_5$ have independently the same meanings as $R_1$ and $R_2$, $R_6$ and $R_7$ have independently the same meanings as $R_1$ and $R_2$, or are independently hydrogen, or together are alkylene having 4 to 6 carbon atoms, or $R_1$ and $R_2$ together and $R_4$ and $R_5$ together are alkylene having 4 to 6 carbon atoms, g is 1 or 2, when g is 1, E is hydrogen, alkyl having 1 to 24 carbon atoms, alkenyl having 2 to 14 carbon atoms, aralkyl having 7 to 15 carbon atoms, hydroxyalkyl having 1 to 12 carbon atoms, alkanoyloxyalkyl having 2 to 24 carbon atoms, alkenoyloxyalkyl having 4 to 21 carbon atoms or benzoyloxyalkyl having 8 to 18 carbon atoms, or when g is 2, E is straight or branched chain alkylene having 2 to 10 carbon atoms.

Preferably each of $R_6$ and $R_7$ are hydrogen.

When $R_1$, $R_2$, $R_4$, $R_5$, $R_6$ and $R_7$ are alkyl, cycloalkyl, alkenyl or aralkyl, they may be defined as follow:

alkyl of 1 to 12 carbon atoms, such as for example, methyl, ethyl, isopropyl, sec-butyl, n-amyl, 2-ethylhexyl, n-decyl or n-dodecyl, preferably alkyl of 1 to 4 carbon atoms, most preferably methyl;

alkenyl of 3 to 8 carbon atoms, such as for example, vinyl, allyl, butenyl, crotyl, octenyl or dodecenyl, preferably allyl;

cycloalkyl of 5 to 12 carbon atoms, such as for example, cyclopentyl, cyclohexyl, cyclooctyl or cyclododecyl, preferably cyclohexyl; and aralkyl or 7 to 15 carbon atoms, such as for example, benzyl, p-methylbenzyl, 4-butylbenzyl, 4-octylbenzyl, preferably benzyl.

$R_3$ may be alkanoyl of 1 to 12 carbon atoms, such as for example, formyl, acetyl, propionyl, butanoyl, valeroyl, caproyl, capryloyl, decanoyl or lauroyl, preferably alkanoyl of 2 to 8 carbon atoms, or $R_3$ may be alkenoyl of 3 or 8 carbon atoms, such as for example, acryloyl, methacryloyl, crotonoyl, hexenoyl or octenoyl, preferably alkenoyl of 3 to 4 carbon atoms.

Most preferably $R_3$ is acetyl, propionyl, acryloyl or benzoyl.

Examples of alkenyl and aralkyl given above for $R_1$ inter alia apply equally for E when E is alkenyl or aralkyl.

When $R_1$ and $R_2$, $R_4$ and $R_5$ or $R_6$ and $R_7$ together are alkylene of 4 to 6 carbon atoms, they are tetramethylene, pentamethylene or hexamethylene.

When E is alkyl of 1 to 24 carbon atoms, alkyl is, for example, methyl, ethyl, isopropyl, n-amyl, 2-ethylhexyl, n-decyl, n-dodecyl, n-hexadecyl, n-octadecyl, eicosyl or tetracosyl. Preferably E is alkyl of 1 to 12 carbon atoms.

When E is hydroxyalkyl of 1 to 12 carbon atoms, E is, for example, hydroxymethyl, 2-hydroxyethyl, 2-hydroxypropyl, 3-hydroxypropyl, 2-hydroxybutyl, or 2-hydroxydodecyl. Preferably E is hydroxyalkyl of 1 to 3 carbon atoms.

When E is alkanoyloxyalkyl of 2 to 24 carbon atoms, E is, for example, formyloxymethyl, acetoxymethyl, 2-acetoxyethyl, 2-butanoyloxyethyl, 2-octanoyloxyethyl, 2-dodecanoyloxyethyl, 3-eicosanoyloxypropyl and the like. Preferably E is alkanoyloxyalkyl of 3 to 14 carbon atoms.

When E is alkenoyloxyalkyl of 4 to 21 carbon atoms, E is, for example, acryloyloxymethyl, 2-acryloyloxyethyl, 2-methacryloyloxyethyl, 2-oleyloxyethyl and the like. Preferably E is alkenoyloxyalkyl of 4 to 7 carbon atoms.

When E is benzoyloxyalkyl of 8 to 18 carbon atoms, E is, for example, benzoyloxymethyl, 2-benzoyloxyethyl, 3-benzoyloxypropyl and the like. Preferably E is benzoyloxyalkyl of 9 to 11 carbon atoms.

When E is alkylene of 2 to 10 carbon atoms, E is, for example, 1,2-propylene, trimethylene, tetramethylene, pentamethylene, hexamethylene, octamethylene or decamethylene. Preferably E is ethylene.

The intermediates needed to prepare the instant compounds are largely items of commerce or are easily prepared by known methods.

The methods for the preparation of many of the starting materials of this invention are set forth in U.S. Pat. No. 4,190,571, the pertinent parts of which are incorporated herein by reference.

The compounds of this invention are effective light stabilizers in a wide range of organic polymers. Polymers which can be stabilized include:

1. Polymers which are derived from mono- or diolefins, e.g., polyethylene which can optionally be cross-linked, polypropylene, polyisobutylene, polymethylbutene-1, polymethylpentene-1, polyisoprene, polybutadiene.

2. Mixtures of the homopolymers cited under 1, for example mixtures of polypropylene and polyethylene, polypropylene and polybutene-1, polypropylene and polyisobutylene.

3. Copolymers of the monomers based on the hompolymers cited under 1, for example ethylene/propylene copolymers, propylene/butene-1, copolymers, propylene/isobutylene copolymers, ethylene/butene-1 copolymers as well as terpolymers of ethylene and propylene with a diene, for example hexadiene, dicyclopentadiene or ethylidene norbornene, and copolymers of α-olefins, e.g., ethylene with acrylic or methacrylic acid.

4. Polystyrene.

5. Copolymers of styrene and of α-methylstyrene, for example styrene/butadiene copolymers, styrene/acrylonitrile copolymers, styrene/acrylonitrile/methacrylate copolymers, styrene/acrylonitrile copolymers modified with acrylic ester polymers to provide impact strength as well as block copolymers, e.g., styrene/butadiene/styrene block copolymers.

6. Graft copolymers of styrene, for example the graft polymer of styrene to polybutadiene, the graft polymer of styrene with acrylonitrile to polybutadiene as well as mixtures thereof with the copolymers cited under 5, commonly referred toas acrylonitrile/butadiene/styrene or ABS plastics.

7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.

8. Polymers which are derived from α, β-unsaturated acids and derivatives thereof, such as polyacrylates and polymethacrylates, polyacrylic amides and polyacrylonitrile.

9. Polymers which are derived from unsaturated alcohols and amines and from the acyl derivatives thereof or acetals, forexample polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.

10. Homopolymers and copolymers which are derived from epoxides, for example polyethylene oxide or the polymers which are derived from bis-glycidyl ethers.

11. Polyacetals, for example polyoxymethylene, as well as polyoxymethylenes which contain ethylene oxide as comonomer.

12. Polyalkylene oxides, for example polyoxyethylene, polypropylene oxide or polybutylene oxide.

13. Polyphenylene oxides.

14. Polyurethanes and polyureas, such as in urethane coatings.

15. Polycarbonates.

16. Polysulfones.

17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenylene-isophthalamide.

18. Polyesters which are derived from dicarboxylic acids and dialcohols and/or from hydroxycarboxylic acids or the corresponding lactones, for example polyethylene glycol terephthalate, poly-1,4-dimethylolcyclohexane terephthalate.

19. Cross-linked polymers which are derived from aldehydeson the one hand and from phenols, ureas and melamine on the other, for example phenol/formaldehyde, urea/formaldehyde and melamine/formaldehyde resins.

20. Alkyd resins, for example glycerol/phthalic acid resins and mixtures thereof with melamine/formaldehyde resins.

21. Unsaturated polyesters resins which are derived from copolyesters of saturated and unsaturated dicarboxylic acids with polyhydric alcohols as well as from vinyl compounds as cross-linking agents and also the halogen-containing, flame-resistant modifications thereof.

22. Natural polymers, for example cellulose, rubber, as well as the chemically modified homologous derivatives thereof, for example cellulose acetates, cellulose propionates and cellulose butyrates and the cellulose ethers, for example methylcellulose.

Although the compounds of this invention are effective stabilizers for polyolefins and other polymeric substrates, they find particular importance as stabilizers for thermoset acrylic or alkyd acrylic resins or enamels.

The instant stabilizers are added to the plastics in a concentration of 0.05 to 5% by weight, calculated relative to the material to be stabilized. Preferably, 0.1 to 2.5% by weight of the stabilizer calculated relative to the material to be stabilized, is incorporated into the latter.

Incorporation can be effected after polymerization, for example by mixing the compounds and, if desired, further additives into the melt by the methods customary in the art, before or during shaping, or by applying the dissolved or dispersed compounds to the polymer, with subsequent evaporation of the solvent if necessary.

The stabilizers can also be added to the plastics to be stabilized in the form of a master batch which contains these compounds, for example in a concentration of 2.5 to 25% by weight.

Although the compounds of the invention may be used to provide a light stabilizing function, the compounds of this invention are often combined with other stabilizers, even other light stabilizers, in the preparation of stabilized compositions. The stabilizers may be used with phenolic antioxidants, pigments, colorants or dyes, light stabilizers such as hindered amines, metal deactivators, etc.

In general, the stabilizers of this invention are employed from about 0.05 to about 5% by weight of the stabilized composition, although this will vary with the particular substrate and application. An advantageous range is from about 0.1 to about 2.5%.

The stabilizers of Formula I may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain from about 0.05 to about 5%, preferably from about 0.1 to about 2.5% by weight of various conventional additives, such as the following, particularly phenolic antioxidants or light-stabilizers, or mixtures thereof:

1. Antioxidants 1.1 Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-diocta-decyl-4-methylphenol.

1.2 Derivatives of alkylated hydroquinones, such as for example, 2,5-di-tert.-butyl-hydroquinone, 2,5-di-tert.-amylhydroquinone, 2,6-di-tert.-butyl-hydroquinone, 2,5-di-tert.butyl-4-hydroxy-anisole, 3,5-di-tert.-butyl-4-hydroxy-anisole, 3,5-di-tert.-butyl-4-hydroxyphenyl stearate and bis-(3,5-ditert.-butyl-4-hydroxyphenyl) adipate.

1.3 Hydroxylated thiodiphenyl ethers, such as for example, 2,2'-thio-bis-(6-tert.-butyl-4-methylphenol), 2,2'-thio-bis-(4-octylphenol),4,4'-thio-bis-(tert.butyl-3-methylphenol), 4,4'-thio-bis-(3,6-di-sec.-amylphenol), 4,4'-thio-bis-(6-tert.- butyl-2-methylphenol) and 4,4'-bis-(2,6-dimethyl-4-hydroxy-phenyl) disulfide.

1.4 Alkylidene-bisphenols, such as for example, 2,2'-methylene-bis-(6-tert.-butyl-4-methylphenol), 2,2'-methylenebis-(6-tert.-butyl-4-ethylphenol), 4,4'-methylene-bis-(6-tert.butyl-2-methylphenol), 4,4'-methylene-bis-(2,6-d-tert.-bitylphenol), 2,6-di-(3-tert.-butyl-5-methyl-2-hydroxybenzyl)-4-methylphenol, 2,2'-methylene-bis-[4-methyl-6-(α-methylcyclohexyl)-phenol], 1,1-bis(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis(5-tert.-butyl-4-hydroxy-2-methylphenyl)-4-n-dodecylmercapto-butane, 1,1,5,5-tetra-(5-tert.-butyl-4-hydroxy-2-methylphenyl)-pentane and ethylene glycol bis-[3,3-bis-(3-tert.-butyl-4-hydroxyphenyl)-butyrate].

1.5 O-, N- and S-benzyl compounds, such as for example, 3,5,3',5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl) dithioterephthalate.

1.6 Hydroxybenzylated malonates, such as for example, dioctadecyl 2,2-bis-(3,5-di-tert.-butyl-2-hydroxybenzyl)-malonate, dioctadecyl 2-(3-tert.-butyl-4-hydroxy-5-methylbenzyl)malonate, di-dodecylmercapto-ethyl 2,2-bis-(3,5-di-tert.-butyl4-hydroxybenzyl)-malonate and di-[4-(1,1,3,3-tetramethylbutyl)phenyl] 2,2-bis-(3,5-di-tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)2,4,6-trimethyl-benzene, 1,4-di-(3,5-di-tert-butyl-4-hydroxybenzyl)-2,3,5,6-tetramethylbenzene and 2,4,6-tri-(3,5-di-tert.-butyl-4-hydroxy-benzyl)-phenol.

1.8 s-Triazine compounds, such as, for example 2,4-bisoctylmercapto-6-(3,5-di-tert.-butyl-4-hydroxyanilino)-s-triazine, 2-octylmercapto-4,6-bis-(3,5-di-tert.-butyl-4hydroxy anilino)-s-triazine, 2-octylmercapto-4,6-bis-(3,5-ditert.-butyl-4-hydroxyphenoxy)-s-triazine, 2,4,6-tris(3,5-di-tert.-butyl-4-hydroxyphenoxy)-s-triazine, 2,4,6-tris(3,5-di-tert.-butyl-4-hydroxphenylethyl)-s-triazine and 1,3,5-tris-(3,5-di-tert.-butyl-4-hydroxybenzyl) isocyanurate.

1.9 Amides of β-(3,5-di-tert.-butyl-4-hydroxyphenyl)-pro-pionic acids, such as, for example 1,3,5-tris-(3,5,-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine, N,N'-bis-β-(3,5-di-t-butyl-4-hydroxyphenyl)propionyl-hydrazine.

1.10 Esters of β-(3,5-di-tert.-butyl-4-hydroxyphenyl)-pro-pionic acid with monohydric or polyhydric alcohols, such as for example, with methanol, ethanol, octadecanol, 1,6-hexanediol;. 1,9-nonanediol, ethylene glycol, 1,2-propane-diol, diethylene glycol, thiodiethylene glycol, neopentylglycol, pentaerythritol,3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2.2.2]octane.

1.11 Esters of β-(5-tert.-butyl-4-hydroxy-3-methylphenyl)-propionic acid with monohydric or polyhydric alcohols, such as for example, with methanol, ethanol, octadecanol, 1,6-hexanediol, 1-9-nonanediol, ethylene glycol, 1,2-propanediol, di- ethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2.]octane.

1.12 Esters of 3,5-di-tert.-butyl-4-hydroxyphenylacetic acid with monohydric or polyhydric alcohols, such as for example, with methanol, ethanol, octadecanol, 1,6-hexandiol, 1,9-nonanediol, ethylene glycol, 1,2-propenediol, diethylene glycol, thiodiethylene glycol, neopentylglycol, pentaerythritol, 3-thia-undecanol, 3-thia-pentadecanol, trimethylhexanediol,trimethylolethane, trimethylolpropane, tris-hydroxyethyl isocyanurate and 4-hydroxymethyl-1-phospha-2,6,7-trioxabicyclo-[2.2.2]-octane, especially the tetrakis ester of pentaerythritol.

1.13 Benzylphosphonates, such as, for example, dimethyl 3,5di-tert.-butyl-4-hydroxybenzylphosphonate, diethyl 3,5-di-tert.-butyl-4-hydroxybenzylphosphonate, dioctadecyl 3,5-di-tert.-butyl-4-hydroxybenzylphosphonate and dioctadecyl 5-tert.-butyl-4-hydroxy-3-methylbenzylphosphonate.

2. Light-stabilizers 2.1 Esters of optionally substituted benzoic acids, e.g., 3,5-di-tert.-butyl-4-hydroxybenzoic acid, 2,4-di-tert.-butylphenyl ester or -octadecyl ester or 2-methyl-4,6-di-tert.-butyl-phenyl ester.

2.2 Sterically hindered amines e.g., 4-benzoyl-2,2,6,6-tetramethylpiperidine, 4-stearyloxy-2,2,6,6-tetramethylpiperidine, bis-(2,2,6,6-tetramethylpiperidyl) sebacate, bis(1,2,2,6,6-pentamethylpiperidyl) sebacate, bis-(1,2,2,6,6-pentamethylpiperidyl) 2-n-butyl-2-(2-hydroxy-3,5-di-tert-butylbenzyl)malonate or 3-n-octyl-7,7,9,9-tetra-methyl-1,3,8-triazaspiro[4.5]decane-2,4-dione.

2.3 Oxalic acid diamides, e.g., 4,4'-di-octyloxy-oxanilide, 2,2'-di-octyloxy-5,5'-di-tert.butyl-oxanilide, 2,2'-didodecycloxy-5,5'-di-tert.-butyl-oxanilide, 2-ethoxy-2'-ethyloxanilide, N,N'-bis-(3-dimethyl-aminopropyl)-oxalamide, 2-ethoxy-5-tert.-butyl-2'-ethyl-oxanilide and the mixture thereof with 2-ethoxy-2'-ethyl-5,4'-di-tert.-butyl-oxanilide, or mixture of ortho- and para-methoxy- as well as of o- and p-ethoxy-disubstituted oxanilides.

3. Metal deactivators, e.g., oxanilide, isophthalic acid dihydrazide, sebacic acid-bis-phenylhydrazide, bis-benzylidene-oxalic acid dihydrazide, N,N'-diacetal-adipic acid dihydrazide, N,N'-bis-salicyloyl-oxalic acid dihydrazide, N,N'-bis-salicyloylhydrazine, N,N'-bis-(3,5-di-tert.-butyl-4-hydroxy-phenylpropionyl)-hydrazine, N-salicyloyl-N'-salicylalhydraxine, 3-salicyloyl-amino-1,2,4-triazole or N,N'-bis-salicyloyl-thiopropionic acid dihydrazide.

4. Basic co-stabilizers, e.g., alkali metal salts and alkaline-earth metal salts of higher fatty acids, for example Ca-stearate, Zn-stearate, Mg-behenate, Na-ricinoleate or K-palmitate.

5. Nucleation agents, e.g., 4-tert.-butylbenzoic acid, adipic acid or diphenylacetic acid.

6. Phosphites and phosphonites, such as, for example, triphenyl phosphite, diphenylalkyl phosphites, phenyldialkyl phosphites, tri-(nonyl-phenyl) phosphite, trilauryl phosphite, trioctadecyl phosphite and 3,9-isodecyloxy-2,4,8,10-tetraoxa3,9-diphospha-[5.5]-undecane and tetra(2,4-di-tert-butylphenyl) diphenylene-4,4'-bis(phosphonite).

Other additives that can be incorporated in the stabilized compositions are thiosynergists such as dilauryl thiodiproprionate, lubricants such as stearyl alcohol, fillers, asbestos, kaolin, talc, glass fibers, pigments, optical brighteners, flameproofing agents and antistatic agents.

The following examples are presented for the purpose of illustration only and are not to be construed to limit the nature or scope of the instant invention in any manner whatsoever.

EXAMPLE 1

1,1'-Ethylenebis(4-acetyl-3,3,5,5-tetramethyl-2-piperazinone)

31.5 grams (0.1 mole) of 1,1'-ethylenebis(3,3,5,5-tetramethyl-2-piperazinone), prepared according to Example 6, E of U.S. Pat. No. 4,190,571 from N,N'-(2-amino-2-methylpropyl)ethylenediamine and acetone cyanohydrin, is dissolved in 102 grams (1.0 mole) of acetic anhydride. After three drops of concentrated sulfuric acid are added to the solution, the mixture is heated for four hours at 130° C. and then cooled to room temperature. Methylene chloride (200 ml.) is added to extract the product into an organic layer which is then washed successively with water and with saturated sodium bicarbonate solution and is finally dried over anhydrous magnesium sulfate. The solvent is removed in vacuo and the residual product is recrystallized from toluene to give 30.4 grams of the above-named product as a white solid, melting at 180°–183° C. (sintering at 170° C.).

Analysis: Calcd for $C_{22}H_{38}N_4O_4$: C, 62.53; H, 9.06; N, 13.26. Found: C, 62.6; H, 9.0; N, 13.4.

The structure is confirmed by nmr.

EXAMPLE 2

1,1'-Ethylenebis(4-propionyl-3,3,5,5-tetramethyl-2-piperazinone)

Following the method of Example 1, the above-named compound is obtained when an equivalent amount of propionic anhydride is substituted for acetic anhydride. The product is recrystallized from heptane-toluene giving a white solid melting at 135°–137° C.

Analysis: Calcd for $C_{24}H_{42}N_4O_4$: C, 64.0; H, 9.4; N, 12.4. Found: C, 64.2; H, 9.6; N, 12.3.

EXAMPLE 3

1,1'-Ethylenebis(4-acryloyl-3,3,5,5-tetramethyl-2-piperazinone)

A solution of 25.0 grams (0.074 moles) of 1,1'-ethylenebis(3,3,5,5-tetramethyl-2-piperazinone), prepared as seen in Example 1, and 31.4 grams (0.31 mole) of triethylamine in 200 ml of 1,2-dichloroethane is cooled to 0° C. To this cooled solution is added over a 30-minute period at 0° C., 19.2 grams (0.15 mole) of 2-chloropropionyl chloride. The resulting mixture is stirred for two hours at 0°–5° C. and then refluxed for two hours. The triethylamine hydrochloride salt formed is removed by filtration and the filtrate is washed successively with 1 N hydrochloric acid, water and brine, and finally dried over anhydrous magnesium sulfate. The solvent is evaporated and the residue recrystallized from heptane-chloroform to give 19.3 grams of the above named product as a white solid melting at 149°–150° C.

Analysis: Calcd for $C_{24}H_{38}N_4O_4$: C, 64.5; H, 8.6; N, 12.5. Found: C, 64.7; H, 8.6; N, 12.4.

The structure is confirmed by nmr and IR.

EXAMPLE 4

Weatherability of Thermoset Acrylic Resin Compositions

A thermoset acrylic enamel composition, used in automotive paint formulations, is stabilized as seen below by incorporation of the indicated stabilizer into the automotive paint. The stabilized composition is then sprayed over a primer on a metallic panel. The panel is then heated for 30 minutes at 250° F. (121° C.) to cure the composition. The initial coating film thickness is 2.5 mils (63 microns, 0.063 mm).

After storage for three weeks in an air-conditioned room (23° C./50% relative humidity), the coated panels are subjected to weathering in the accelerated (quick) weathering test (QUV) involving alternating 1-hour periods of UV irradiation at 70° C. with a 4-hour period of condensation (rain) at 50° C. for each cycle for a total of 730 hours. (ASTM G-53/77)

Gloss values (20° gloss) as measured by ASTM D-523 using a standard glossmeter or goniophotometer and Distinctness of Image (DI) (ASTM D-16), measured using a spectrophotometer, are measured on the coating surface before exposure and after exposure in the OUV test. The results are given in the table below and are expressed in % of the property retained after exposure.

| Stabilizer[a], | % Retention of Property after Exposure in QUV | |
| --- | --- | --- |
| (% by weight) | 20° gloss | DI |
| None | 4 | 11 |

-continued

| Stabilizer$^a$, (% by weight) | % Retention of Property after Exposure in QUV | |
|---|---|---|
| | 20° gloss | DI |
| Compound of Example 2 (2%) | 4 | 28 |
| Compound of Example 3 (2%) | 61 | 54 |
| Stabilizer A (2%) | 6 | 6 |

$^a$Stabilizer A is N—phenyl-N—ethyl-N'—p-carbethoxyphenylformamidine

The thermoset acrylic is based on a binder of 70% of acrylic monomers such as hydroxyethyl acrylate, styrene, acrylonitrile, butyl acrylate and acrylic acid with 30% of a melamine resin, such as hexamethoxymethyl melamine.

Clearly the instant compounds of Examples 2 and 3, particularly the compound of Example 3, are effective stabilizers for protecting thermoset acrylic resins from the adverse effects of weathering.

EXAMPLE 5

Knoop Hardness and Appearance of Resins on Storage

To the thermoset acrylic enamel composition described in Example 4 is added 0.1% by weight of p-toluenesulfonic acid as a curing catalyst. Each composition contained 2% by weight of a test stabilizer. The catalyzed enamel is applied to a steel panel and baked for 60 minutes at 250° F. (121° C.). After storage at ambient conditions for one week, the coated panel is evaluated for hardness using the Knoop test (ASTM B-578) using a Knoop indenter and for general appearance. The results are given below.

| 2% by Weight Stabilizer$^a$ | Knoop Hardness Number | Coating Appearance |
|---|---|---|
| None | 8.0 | Clear |
| Stabilizer B | 1.0 | Precipitate present, opaque |
| Compound of Example 1 | 7.0 | Clear |
| Compound of Example 2 | 8.0 | Clear |
| Compound of Example 3 | 8.0 | Clear |

$^a$Stabilizer B is di(2,2,6,6-tetramethylpiperidin-4-yl)sebacate.

The compounds of this invention are soluble in the thermoset acrylic resin giving a clear, uniform cured coating with excellent hardness. (Knoop hardness numbers increase with increasing hardness of the coating.)

What is claimed is:

1. A composition of matter comprising an organic polymer which is a thermoset acrylic or alkyd acrylic resin or enamel subject to light-induced deterioration stabilized with from 0.05 to 5% by weight of a compound of formula I $$(T-)_g E \qquad (I)$$

wherein
T is a group of the formula

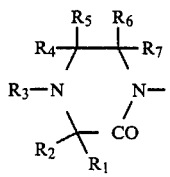

$R_1$ and $R_2$ are independently alkyl having 1 to 12 carbon atoms, cycloalkyl having 5 to 12 carbon atoms, alkenyl having 2 to 14 carbon atoms or aralkyl having 7 to 15 carbon atoms,
$R_3$ is alkanoyl having 1 to 12 carbon atoms, alkenoyl having 3 to 8 carbon atoms or benzoyl,
$R_4$ and $R_5$ have independently the same meanings as $R_1$ and $R_2$,
$R_6$ and $R_7$ have independently the same meanings as $R_1$ and $R_2$, or are independently hydrogen, or together are alkylene having 4 to 6 carbon atoms, or
$R_1$ and $R_2$ together and $R_4$ and $R_5$ together are alkylene having 4 to 6 carbon atoms,
g is 1 or 2,
when g is 1, E is hydrogen, alkyl having 1 to 24 carbon atoms, alkenyl having 2 to 14 carbon atoms, aralkyl having 7 to 15 carbon atoms, hydroxyalkyl having 1 to 12 carbon atoms, alkanoyloxyalkyl having 2 to 24 carbon atoms, alkenoyloxyalkyl having 4 to 21 carbon atoms or benzoyloxyalkyl having 8 to 18 carbon atoms, or
when g is 2, E is straight or branched chain alkylene having 2 to 10 carbon atoms.

2. A composition according to claim 1 wherein the organic polymer is a thermoset acrylic resin or enamel.

3. A composition according to claim 1 wherein the compound is 1,1'-ethylenebis(4-acryloyl-3,3,5,5-tetramethyl-2-piperazinone).

4. A method of stabilizing an organic polymer which is a thermoset acrylic or alkyd acrylic resin or enamel subject to light-induced deterioration by the addition of from 0.05 to 5% by weight of a compound of formula I $$(T-)_g E \qquad (I)$$

wherein
T is a group of the formula

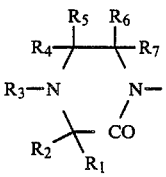

$R_1$ and $R_2$ are independently alkyl having 1 to 12 carbon atoms, cycloalkyl having 5 to 12 carbon atoms, alkenyl having 2 to 14 carbon atoms or aralkyl having 7 to 15 carbon atoms,
$R_3$ is alkanoyl having 1 to 12 carbon atoms, alkenoyl having 3 to 8 carbon atoms or benzoyl,
$R_4$ and $R_5$ have independently the same meanings as $R_1$ and $R_2$,
$R_6$ and $R_7$ have independently the same meanings as $R_1$ and $R_2$, or are independently hydrogen, or together are alkylene having 4 to 6 carbon atoms, or
$R_1$ and $R_2$ together and $R_4$ and $R_5$ together are alkylene having 4 to 6 carbon atoms,
g is 1 or 2,
when g is 1, E is hydrogen, alkyl having 1 to 24 carbon atoms, alkenyl having 2 to 14 carbon atoms, aralkyl having 7 to 15 carbon atoms, hydroxyalkyl having 1 to 12 carbon atoms, alkanoyloxyalkyl having 2 to 24 carbon atoms, alkenoyloxyalkyl having 4 to 21 carbon atoms or benzoyloxyalkyl having 8 to 18 carbon atoms, or
when g is 2, E is straight or branched chain alkylene having 2 to 10 carbon atoms.

5. A method according to claim 4 in which the organic polymer is a thermoset acrylic resin or enamel.

6. A method according to claim 4 wherein the compound is 1,1'-ethylenebis(4-acryloyl-3,3,5,5-tetramethyl-2-piperazinone).

* * * * *